United States Patent

Brophy et al.

Patent Number: 5,970,434
Date of Patent: Oct. 19, 1999

[54] METHOD FOR DETERMINING AVERAGE WALL THICKNESS FOR PIPES AND TUBES USING GUIDED WAVES

[75] Inventors: Joseph W. Brophy; Hegeon Kwun, both of San Antonio, Tex.

[73] Assignee: Southwest Research Institute, San Antonio, Tex.

[21] Appl. No.: 09/015,133

[22] Filed: Jan. 29, 1998

[51] Int. Cl.[6] .................................................. G01N 29/00
[52] U.S. Cl. .............................. 702/170; 73/584; 73/620; 73/627; 324/220
[58] Field of Search .............................. 702/170; 73/584, 73/622, 620, 625, 629, 632, 628, 627; 324/220, 226

[56] References Cited

U.S. PATENT DOCUMENTS

| | | | |
|---|---|---|---|
| 4,037,465 | 7/1977 | Cook et al. | 73/588 |
| 4,265,025 | 5/1981 | Finlayson et al. | 33/178 F |
| 4,669,310 | 6/1987 | Lester | 73/597 |
| 4,685,334 | 8/1987 | Latimer | 73/599 |
| 4,909,080 | 3/1990 | Kikuta et al. | 73/290 V |
| 5,092,176 | 3/1992 | Buttram et al. | 73/599 |
| 5,418,823 | 5/1995 | Kervinen et al. | 73/622 |

Primary Examiner—John Barlow
Assistant Examiner—Hien Vo
Attorney, Agent, or Firm—Kammer & Huff, PLLC

[57] ABSTRACT

A method for determining changes in the average wall thickness or the mean radius of a pipe or tube using ultrasonic and/or magnetostrictive wave probes by analyzing the dispersive behavior of waves traveling in the tube wall volume. The method examines certain wave propagation modes and identifies a cut-off frequency that is characteristic for a particular wall thickness or tube diameter. This method permits the rapid and accurate inspection of a length of pipe or tube from a single location on the inside diameter of the pipe and permits a comparison of data gathered with similar data for the structure in its original condition. Changes in the cut-off frequency, indirectly determined by the method of the present invention are inversely related to changes in the wall thickness and/or the mean radius for the cylindrical structure. In this manner the method of the present invention provides a mechanism for determining the remaining service life for such pipes and tubes.

8 Claims, 3 Drawing Sheets

METHOD FOR DETERMINING AVERAGE WALL THICKNESS FOR PIPES AND TUBES USING GUIDED WAVES

BACKGROUND OF THE INVENTION

1. Field of the Invention

The present invention relates generally to methods for the non-destructive evaluation of the condition of pipes, tubes, cylindrical shells and the like. More specifically, the present invention relates to a method for determining the mean radius of a pipe or tube using guided mechanical waves from a single location on the tubular wall structure.

2. Description of the Related Art

Many industrial structures, frames, conduits, flow columns and the like, are constructed in cylindrical configurations that are often difficult to access. Nonetheless, there is a strong interest in the industry to carry out inspections of such pipe and tube structures for the purpose of determining their remaining life or the nature of any maintenance requirements. Frequently these inspection methods involve the use of non-destructive evaluation (NDE) techniques that are applied to the inside diameter (ID) of the tube or pipe to determine the remaining wall thickness for the structure. Traditional inspection methods generally require an ID probe that is pulled or pushed through the pipe or tube in a progressive manner. Thickness data is acquired from a sequence of incremental positions within the tube or pipe.

There are, however, many environments where an entire length of pipe is not easily accessible from the inside diameter. Some NDE methods are capable of operating on the outer wall of such pipes and tubes but frequently such outer walls are even less accessible than the inside diameter. Heat exchangers are good examples of structural environments where the entire length of a pipe or tube that requires inspection is not accessible. These structures typically involve tube sheets that incorporate sometimes hundreds of U-shaped lengths of tubing. This makes both the interior and exterior walls of the tubing difficult to access for inspection purposes. In many instances the only access points are the terminals of the tubing that are presented at the surface of the tube sheet. It would be difficult to carry out any type of progressive inspection technique in such a structural environment.

In addition to problems with accessibility, progressive inspection techniques often result in large quantities of data that must first be analyzed to determine discrete wall thickness values for a range of locations in the pipe wall. While in some instances this discrete information might be relevant, it is more often the case that an average wall thickness is the desired quantity for determining the remaining service life of a pipe or tube system. Taking a range of values for discrete locations within a pipe or tube and then averaging those values to obtain a quantity for the entire pipe or tube becomes a burdensome task when it is only an average value that is desired from the start.

When the inside diameter of a pipe or tube is accessible, ultrasonic waves and/or magnetostrictively induced mechanical waves can be used to inspect the pipe or tube wall for a determination of the average wall thickness. The types of waves most suitable for an inspection down the length of a target tube are those that propagate longitudinally through the walls using the walls as a wave guide. If these waves could be generated from a single location and could be analyzed from the same or a nearby location, then the goal of acquiring information on the average wall thickness could be more easily achieved.

In general, it would be desirable to carry out inspections of various industrial pipes and tubes from a single location on the inside diameter of the structure. It would be desirable to achieve such an inspection with the goal of obtaining an average thickness or mean radius value that permits an inference of the remaining life of the tube or pipe structure. It would be desirable to achieve such an inspection using familiar inspection techniques such as ultrasonic and magnetostrictive interrogation probes. It would be desirable if a single analysis of wave propagation within a length of pipe could be used to determine the average wall thickness for that length of pipe.

Even with existing techniques for the inspection and determination of wall thicknesses in pipes and tubes, it is often desirable to have some baseline information about the original geometries of the pipe or tube. In this manner, deviations from a baseline value for wall thickness at each discrete test point can be used to calculate the wall thinning that may have occurred at that point. In a system that attempts to measure average wall thickness from a single point on the inside diameter of a pipe or tube, it would also be desirable to have baseline data to facilitate a comparison and the calculation of a new wall thickness average.

SUMMARY OF THE INVENTION

It is therefore an object of the present invention to provide a method for determining the average wall thickness and/or the mean radius of a pipe or tube from a single location on the inside diameter of the structure.

It is another object of the present invention to permit the inspection of a length of pipe or tube for the purpose of determining the remaining life of the structure, by quantifying a change in the average wall thickness for the entire length of pipe or tube.

It is a further object of the present invention to quantify a change in the average wall thickness for an entire length of pipe or tube under inspection, through the use of standard NDE devices for injecting and detecting ultrasonic and other mechanical waves on the inside wall of the pipe or tube at a single location.

It is a further object of the present invention to permit the inspection of an entire length of pipe or tube from a single location on the inside wall of the pipe or tube in order to eliminate the need to progressively test the structure at a large number of locations.

In fulfillment of these and other objectives, the present invention provides a method for determining the average wall thickness, or the mean radius of a pipe or tube, using guided ultrasonic and/or magnetostrictive wave probes by analyzing the behavior of waves traveling in the tube wall. The method of the present invention examines certain longitudinal wave propagation modes and identifies a cut-off frequency that is characteristic for a particular wall thickness or tube radius. The method of the present invention permits the rapid and accurate inspection of a length of pipe or tube from a single location on the inside diameter of the tube and permits a comparison of the data gathered with similar data for the structure in its original condition. Changes in the cut-off frequency, indirectly determined by the method of the present invention, are correlated to changes in the wall thickness and/or mean radius for the cylindrical structure. In this manner the method of the present invention provides a mechanism for determining the remaining service life for such pipes and tubes.

DESCRIPTION OF THE PREFERRED EMBODIMENT

Figure 1:
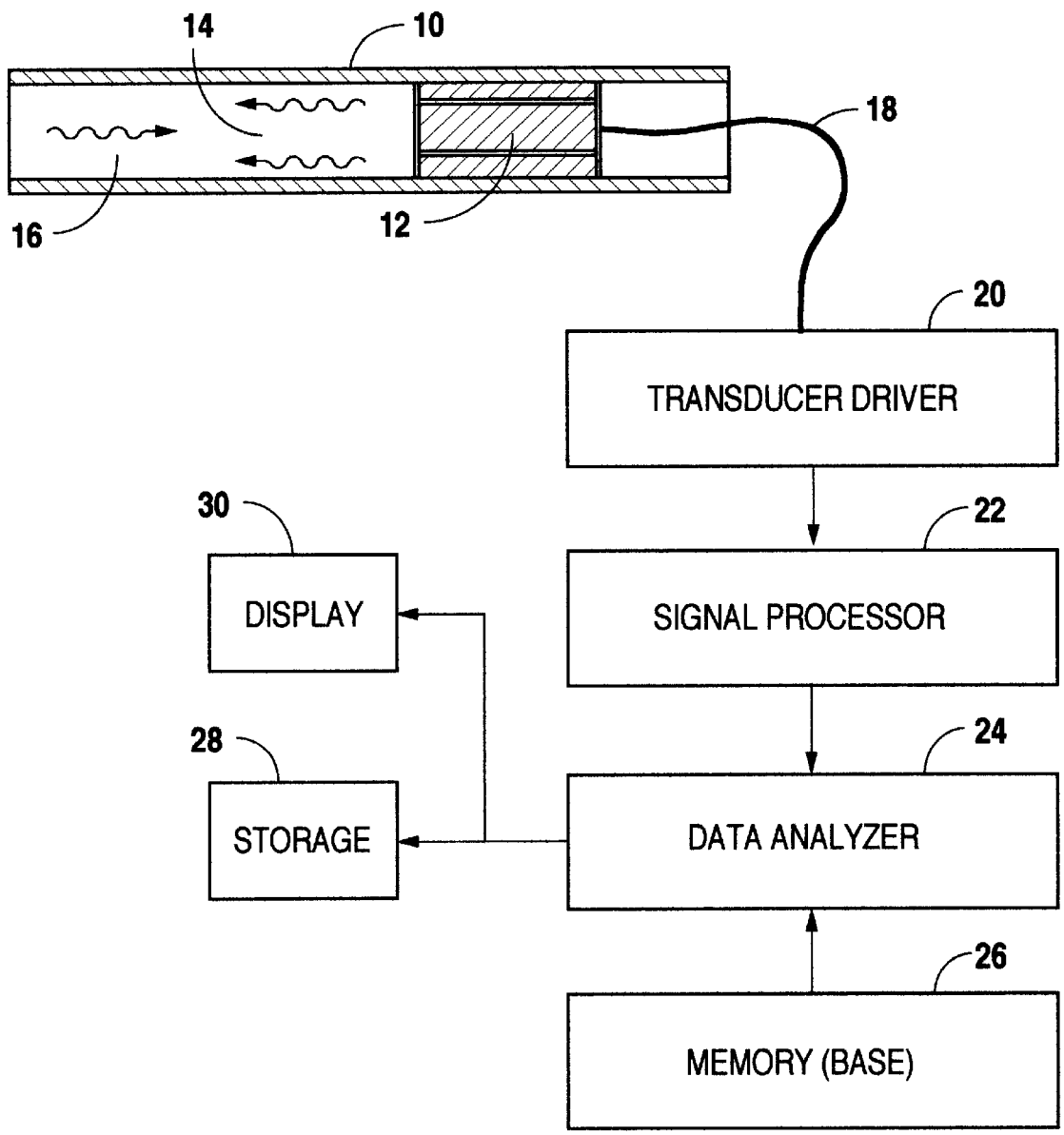
FIG. 1 discloses in schematic form the fundamental components of an NDE inspection system appropriate for implementation of the method of the present invention.

Reference is made first to FIG. 1 for a detailed description of the essential elements of an NDE system appropriate for carrying out the method of the present invention.

FIG. 1 discloses a target pipe/tube (10) with a typical ultrasonic transducer (12) positioned in contact with the inside diameter of tube (10). Transducer (12) could be any of a number of different types of mechanical wave generating transducers that might be piezoelectrically based, magnetostrictively based, or a variety of other such devices. Transducer (12) generates a longitudinal wave set (14) into the walls of pipe/tube (10) to which it is mechanically coupled. Transducer (12) likewise detects a return signal (16) resulting from the dispersion of the interrogating signal (14) into the volume of the walls of pipe/tube (10).

Transducer (12) is driven by transducer driver (20) which directs the frequency and amplitude of the interrogating signal and relays the return signal through transducer cable (18). Driver (20) provides the return signal to signal processor (22) which amplifies and filters the signal for analysis. Data analyzer (24) compares the amplified return signal with stored signal characteristics for baseline geometries for the particular pipe/tube (10) under inspection. Stored baseline signal characteristics are maintained in memory device (26) and may include a number of known geometries and wall thickness structures that might be encountered.

Signal processor (22) in the preferred embodiment of the present invention may establish a digital signal from the frequency, timing, and amplitude characteristics of the return signal from transducer driver (20). Whether in analog or digital form, data analyzer (24) may apply any of a number of well-known signal processing techniques in order to identify and quantify changes in signal propagation characteristics that are indicative of changes in wall thickness. As is described in more detail below, a variety of signal characteristics related to group velocity and frequency allow determination of changes in the cut-off frequency for the particular tubular structure under inspection. As an example, data analyzer (24) may compare the ratio of group velocities at predetermined discrete frequencies for the target pipe/tube under inspection with the baseline for that structure as is described in more detail below. Changes in this ratio are correlated to changes in the average wall thickness (or mean radius) for the pipe/tube. In this manner the extent of wall deterioration and/or the remaining service life of the pipe can be determined.

As indicated above, the present invention demonstrates that the mean radius of a section of tube or pipe can be determined from a single location by analyzing the behavior of acoustic and/or mechanical waves traveling in the tube wall volume. This testing process, referred to as Mean Radius Testing (MRT) is dependent on the dispersion properties of longitudinal, guided waves, propagating in the tube wall. Longitudinal mode guided waves exhibit a characteristic "cut-off" frequency for a specific tube diameter and wall thickness. The frequency range over which a certain wave mode can not propagate is called the "cut-off" frequency. The frequencies at which the cut-off behavior occur depend primarily on the mean radius of the tube or pipe. The behavior is best seen on a dispersion curve displaying each type of propagation mode as a function of group velocity versus signal frequency.

Figure 2:
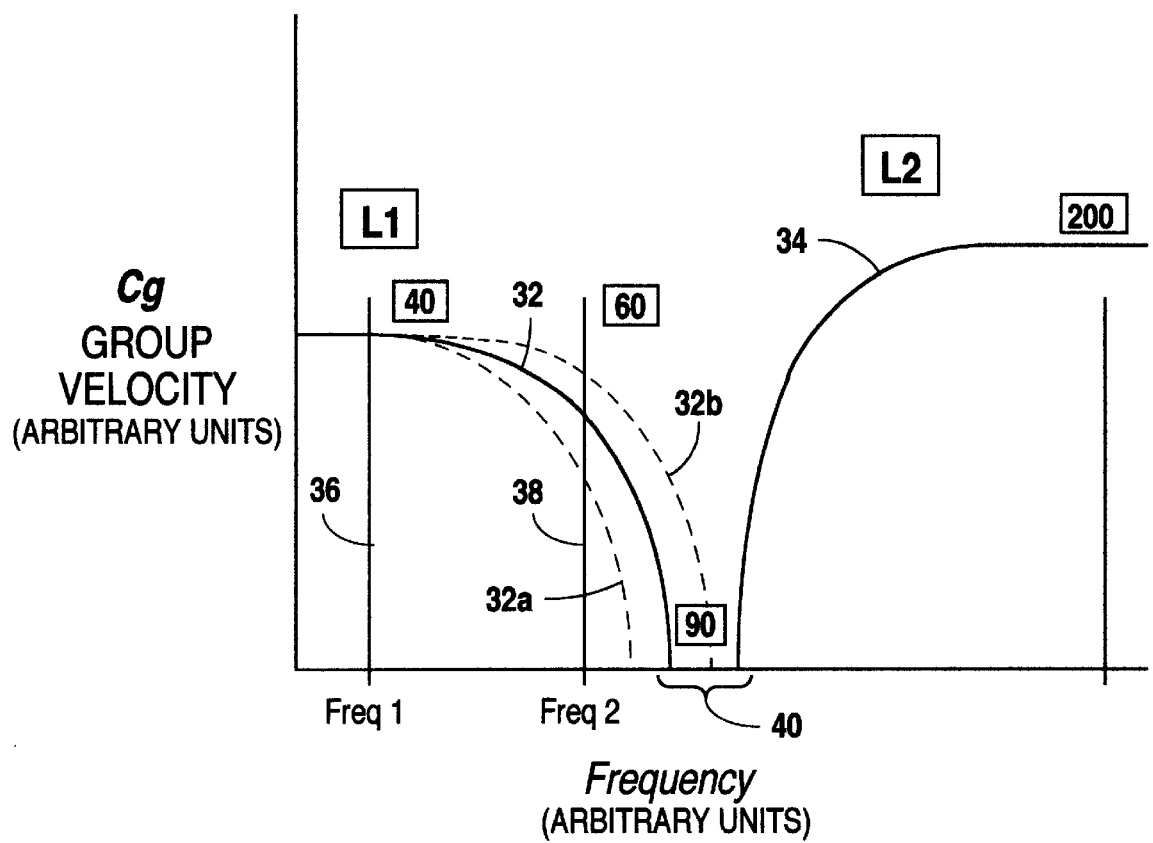
FIG. 2 discloses a sample plot of longitudinal wave propagation showing group velocity as a function of frequency.

FIG. 2 shows an idealized dispersion curve (32) and (34), for the L(0,1) and L(0,2) longitudinal propagation modes. As indicated in the graph, the guided wave group velocity changes significantly as a function of frequency for specific modes. There is a region (40) on the dispersion curve where certain guided wave propagation modes are severely attenuated.

There is an inverse relationship between the cut-off frequency indicated in a plot such as is disclosed in FIG. 2 and the mean radius of the pipe or tube under investigation. The cut-off frequency for the L(0,1) mode is given by the following equation:

$$F_c = V/2\pi B$$

Where $F_c$=the cut-off frequency; V=the Rod velocity limit; and B=the mean radius of the tube.

As can be seen in FIG. 2, the velocity of a guided wave at frequencies (36) significantly lower than the cut-off will be different from the velocity at frequencies (38) closer to the cut-off. The ratio of the velocity at two discrete frequencies for a tube with a given mean radius will be a constant.

The group velocity of the dispersed signal is a function of the frequency and the wall thickness of the pipe or tube. As indicated above, changes in the group velocity can be measured in a number of different ways by analyzing the frequencies and timing of the return signal. The method of the present invention depends upon the establishment of base line return signal characteristics for a particular pipe or tube geometry. Any of a number of analytical methods for determining a shift in the cut-off frequency for a particular structure can then be applied to determine the mean radius of the pipe or tube under investigation. Again referring to FIG. 2, the data analysis could focus on directly determining a shift in the cut-off frequency or indirectly determining the same through an analysis of portions of the dispersion curve. An increase in the mean radius of a pipe or tube as a result of corrosion on the inside surface will, for example, produce a reduction (32a) in the cut-off frequency. This reduction can be exhibited by either the detection of a new value for the cut-off frequency or the detection of a greater slope to the curve at a specific frequency (38).

Likewise, a decrease in the mean radius of a pipe or tube under inspection, which is typically indicative of exterior corrosion on the pipe or tube, will result in a positive shift (32b) in the cut-off frequency that may be evidenced by a decrease in the slope at a specific frequency (38). The slope of the dispersion curve may, of course, be determined by any of a number of finite ratio techniques for analyzing the signal data.

When the wall thickness of a tube changes from a nominal value due to corrosion or other wall loss mechanisms, the mean radius changes. Measuring the velocity at the same two discrete frequencies will produce a ratio different from that obtained for a tube with no mean radius changes. By comparing the velocity ratio from a tube with known dimensions with the velocity ratio from a tube with an undetermined amount of wall loss, the mean radius of the tube can be calculated and from this the average wall loss can be estimated.

Figure 3:
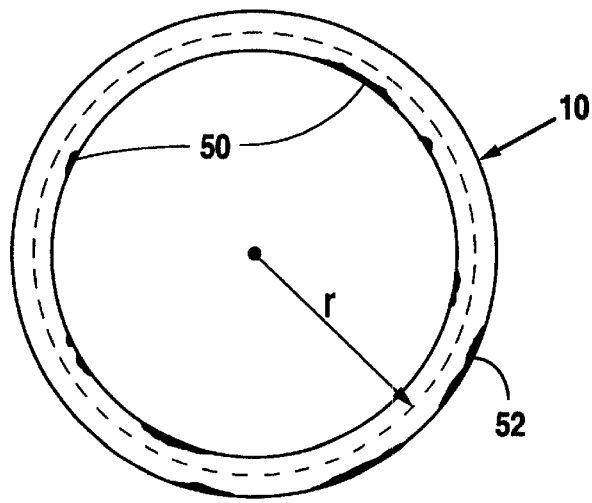
FIG. 3 is a cross-sectional diagram of a typical pipe or tube showing the mean radius and wall deterioration characteristics.

Reference is made to FIG. 3 for a description of the structural geometries associated with the method of the present invention. FIG. 3 discloses in cross-sectional detail pipe/tube (10) having an outside diameter, an inside diameter, and a mean radius R. The outside diameter exhibits some areas of deterioration (52) which serve to reduce the mean radius of the tube. Likewise, the inside diameter exhibits some areas (50) of deterioration which serves to increase the mean radius of the tube.

The primary value of this method of measurement is that the operating condition of the tube can be determined from a single location. The dispersion characteristics of the guided wave can be used (by way of the above equation) to calculate the mean radius of the tube, which can then be used to estimate the remaining average wall thickness.

Figure 4:
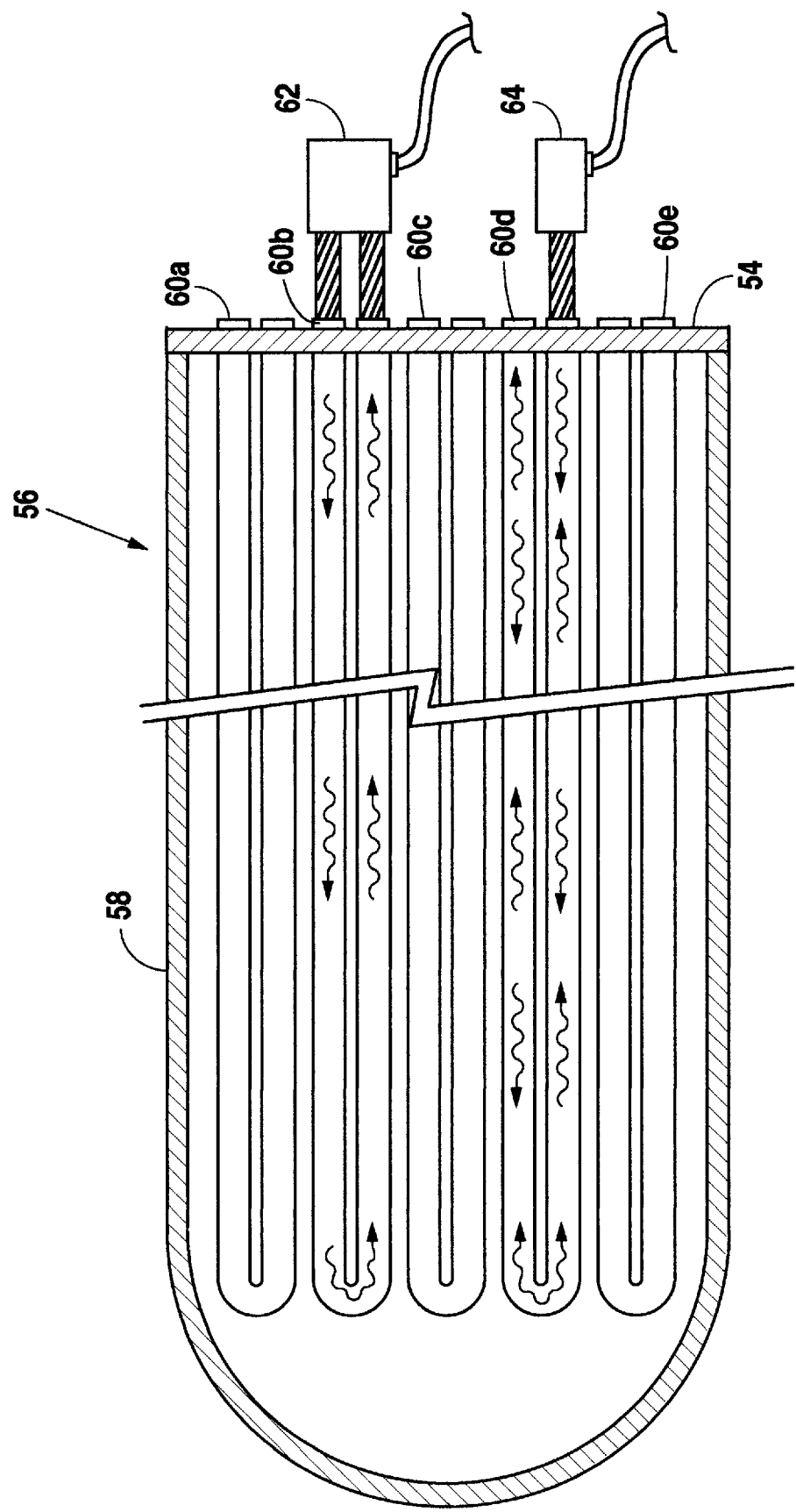
FIG. 4 is a partial cross-sectional view of a typical heat exchanger/tube sheet system that might employ the method of the present invention.

Reference is now made to FIG. 4 for an example of an application of the method of the present invention for the inspection of a typical tubular structure environment. FIG. 4 shows in partial cross-section the structure of a heat exchanger (56) that incorporates a tube sheet (54) positioned within an enclosing shell (58). Tube sheet (54) comprises an array of U-shaped lengths of tubing (60a through 60e). The function of a typical heat exchanger involves the flow of thermal energy from one medium present within shell (58) into or out of a second medium which flows within tubing (60a through 60e).

The inspection of these tubes (60a through 60e) can be carried out according to the method of the present invention from the single access points present on tube sheet (54). A first application of the method of the present invention might involve a pitch-catch technique as is well-known in the field and is shown in FIG. 4 through the use of probe (62). Probe (62) incorporates an appropriately positioned signal source and a separate discrete signal detector. Probe (62) injects an interrogating signal into one end of tube (60b) which signal is received back by probe (62) upon its arrival at the opposite end of tube (60b). The signal will have therefore traveled the entire length of tube (60b) and will exhibit appropriate dispersion characteristics suitable for analyzing changes in the wall thickness of the tube.

A second application of the method of the present invention is shown in FIG. 4 with probe (64). Probe (64) operates according to the pulse-echo method described in conjunction with FIG. 1 above wherein a single transducer device generates the interrogating signal and receives back the return signal. In this case the return signal may be reflected by any of a number of geometric characteristics for the tube, most prominently the terminal end of tube (60d). With either method described, the dispersion characteristics of the signal can be detected and analyzed according to the present method in order to determine shifts in the cut-off frequency that develop over time as a result of wall deterioration.

It is understood that the method of the present invention lends itself to use with a number of different NDE techniques and is not limited to the NDE system described in the preferred embodiment. Various mechanisms for generating mechanical waves within the wall of the pipe or tube are possible and readily exhibit the dispersion characteristics that the present method utilizes. While there may be optimal wave frequencies and amplitudes for generating discernable dispersion patterns, these optimal values are dependent upon the geometry of the pipe or tube under inspection. It is anticipated that such optimal inspection parameters would be determined and set when a priori baseline data regarding a particular structure is acquired.

We claim:

1. A method for measuring changes in an average wall thickness for a longitudinal section of pipe from a single location comprising the steps of:

directing interrogating mechanical waves into a wall of said pipe at said single location;

receiving a multifrequency return signal, said multifrequency return signal resulting from a dispersion of said interrogating mechanical waves throughout said longitudinal section of pipe;

analyzing said return signal by determining the ratio of wave group velocity at a first selected frequency to wave group velocity at a second selected frequency, said first and second selected frequencies being discrete frequencies offset from a cut-off frequency, said cut-off frequency being a frequency range over which said return signal is significantly attenuated due to the original geometry of said pipe;

comparing said ratio of wave group velocities with a baseline ratio for said pipe; and correlating a change in said ratio with a respective change in said average wall thickness for said longitudinal section of pipe.

2. The method of claim 1 wherein said step of analyzing said return signal further comprises analyzing the L(0,1) and L(0,2) longitudinal propagation modes for said dispersion of said interrogating mechanical waves.

3. The method of claim 1 wherein said first selected frequency is significantly less than said cut-off frequency and said second selected frequency is close to said cut-off frequency.

4. The method of claim 1 wherein said step of directing interrogating mechanical waves comprises placing an ultrasonic transducer in mechanical contact with an inside wall of said pipe and driving said transducer with an AC electrical signal.

5. The method of claim 1 wherein said step of directing interrogating mechanical waves comprises positioning a magnetostrictive transducer in proximity to an inside wall of said pipe and driving said transducer with an AC electrical signal.

6. A method for measuring changes in an average wall thickness for a longitudinal section of pipe from a single location on said longitudinal section of pipe, comprising the steps of:

directing interrogating mechanical waves into an inside wall of said pipe;

receiving a multifrequency return signal, said multifrequency return signal resulting from a dispersion of said interrogating mechanical waves throughout said longitudinal section of pipe;

analyzing said return signal by determining a shift in a cut-off frequency identified within said return signal, said cut-off frequency being a frequency range over which said return signal is significantly attenuated due to the original geometry of said pipe;

correlating said shift in said cut-off frequency with a respective change in said average wall thickness for said longitudinal section of pipe.

7. The method of claim 6 wherein said step of analyzing said return signal further comprises determining said shift in said cut-off frequency by analyzing the L(0,1) and L(0,2) longitudinal propagation modes for said dispersion of said interrogating mechanical waves.

8. The method of claim 6 further comprising the step of initially determining said cut-off frequency for said length of pipe by calculating said cut-off frequency according to the equation; $F_c = V/2\pi B$; wherein $F_c$ is the cut-off frequency; V is the Rod velocity limit; and B is the mean radius of said pipe.

* * * * *